United States Patent
Lim et al.

(10) Patent No.: US 11,362,240 B2
(45) Date of Patent: Jun. 14, 2022

(54) LIGHT-EMITTING DEVICE AND METHOD OF PRODUCING A LIGHT-EMITTING DEVICE

(71) Applicant: OSRAM Opto Semiconductors GmbH, Regensburg (DE)

(72) Inventors: Choon Kim Lim, Bayan Baru (MY); Choo Kean Lim, Penang (MY); Hui Chiang Teoh, Jitra (MY)

(73) Assignee: OSRAM Opto Semiconductors GmbH, Regensburg (DE)

( * ) Notice: Subject to any disclaimer, the term of this patent is extended or adjusted under 35 U.S.C. 154(b) by 458 days.

(21) Appl. No.: 16/616,126

(22) PCT Filed: May 24, 2017

(86) PCT No.: PCT/EP2017/062646
§ 371 (c)(1),
(2) Date: Nov. 22, 2019

(87) PCT Pub. No.: WO2018/215068
PCT Pub. Date: Nov. 29, 2018

(65) Prior Publication Data
US 2020/0105983 A1    Apr. 2, 2020

(51) Int. Cl.
| | | |
|---|---|---|
| H01L 33/50 | (2010.01) | |
| A61L 2/10 | (2006.01) | |
| A61L 2/26 | (2006.01) | |
| C09K 11/08 | (2006.01) | |
| A61N 5/06 | (2006.01) | |

(52) U.S. Cl.
CPC ............. *H01L 33/505* (2013.01); *A61L 2/10* (2013.01); *A61L 2/26* (2013.01); *C09K 11/08* (2013.01); *H01L 33/502* (2013.01); *A61L 2202/11* (2013.01); *A61N 5/06* (2013.01); *A61N 2005/0661* (2013.01); *H01L 2933/0033* (2013.01); *H01L 2933/0041* (2013.01)

(58) Field of Classification Search
CPC .......... H01L 33/505; H01L 33/502; A61L 2/10
USPC ............................................................ 257/98
See application file for complete search history.

(56) References Cited

U.S. PATENT DOCUMENTS

| | | | | |
|---|---|---|---|---|
| 6,635,363 | B1 * | 10/2003 | Duclos | .................... H01L 24/32 |
| | | | | 428/917 |
| 7,847,302 | B2 * | 12/2010 | Basin | .................... H01L 33/504 |
| | | | | 257/E33.059 |
| 8,659,043 | B1 * | 2/2014 | Tischler | .................. H01L 33/32 |
| | | | | 257/98 |
| 2010/0283062 | A1 | 11/2010 | Hsieh et al. | |
| 2013/0187178 | A1 | 7/2013 | Tischler | |
| 2015/0300577 | A1 | 10/2015 | Van Bommel et al. | |
| 2017/0025582 | A1 * | 1/2017 | Dai | ........................ H01L 33/502 |

FOREIGN PATENT DOCUMENTS

| | | |
|---|---|---|
| EP | 1 964 906 | 9/2008 |
| EP | 2 549 330 | 1/2013 |

* cited by examiner

*Primary Examiner* — Christopher M Raabe
(74) *Attorney, Agent, or Firm* — DLA Piper LLP (US)

(57) ABSTRACT

The invention refers to a light emitting device including a semiconductor chip having a main radiation surface, which emits UV light in operation, a phosphor, which is arranged in the radiation beam of the UV light, absorbs partially the UV light, wherein the phosphor converts the UV light into visible light so that the device emits mixed light comprising the UV light as well as visible light.

19 Claims, 3 Drawing Sheets

LIGHT-EMITTING DEVICE AND METHOD OF PRODUCING A LIGHT-EMITTING DEVICE

TECHNICAL FIELD

This disclosure relates to a light-emitting device and a method of producing a light-emitting device.

BACKGROUND

It could be helpful to provide a light-emitting device having good properties for use in medical applications or as an indicator showing the operational capability as well as to produce a light-emitting device.

It could also be helpful to produce a light-emitting device having good properties for use in medical applications or as an indicator showing the operational capability.

SUMMARY

We provide a light emitting device including a semiconductor chip having a main radiation surface and side surfaces that emits UV light via the main radiation surface in operation, and a phosphor arranged in the radiation beam of the UV light at the side surfaces, absorbs partially the UV light, wherein the phosphor converts the UV light into visible light so that the device emits mixed light including the UV light as well as visible light, the visible light is emitted via the side surfaces and the UV light is emitted via the main radiation surface, and the visible light is an indicator showing the operational capability of the device for the user.

We also provide a medical device including the light emitting device including a semiconductor chip having a main radiation surface and side surfaces that emit UV light via the main radiation surface in operation, and a phosphor arranged in the radiation beam of the UV light at the side surfaces, absorbs partially the UV light, wherein the phosphor converts the UV light into visible light so that the device emits mixed light including the UV light as well as visible light, the visible light is emitted via the side surfaces and the UV light is emitted via the main radiation surface, and the visible light is an indicator showing the operational capability of the device for the user.

We further provide a method of producing a light emitting device including A) applying at least two semiconductor chips on a substrate, each of the two semiconductor chips having a main radiation surface and side surfaces, B) applying a UV tape on the main radiation surfaces, C) filling a phosphor between neighboring semiconductor chips so that the phosphor forms a frame around the side surfaces of each semiconductor chip, D) removing the UV tape, and E) singulating the assembly.

Figure 1:
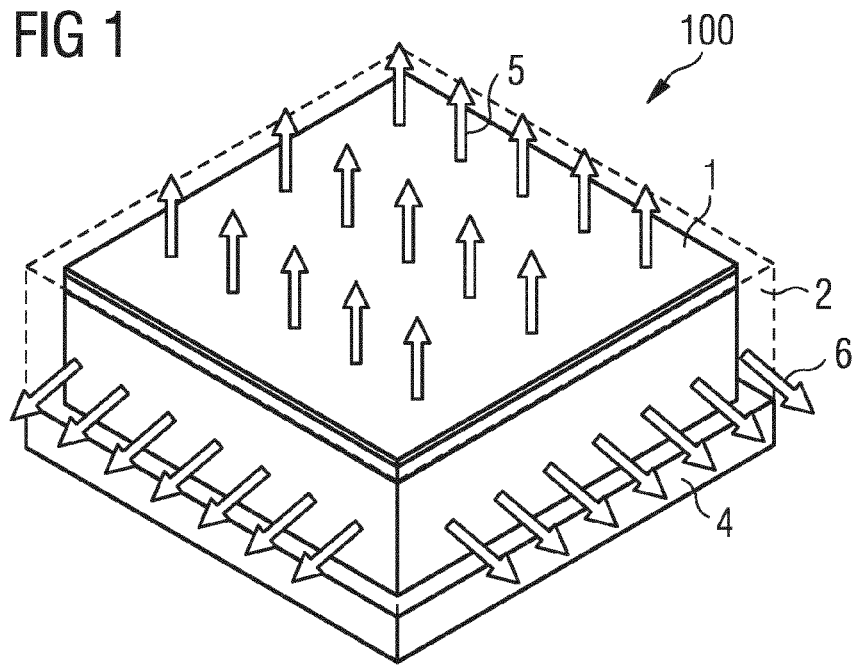
FIGS. 1 and 2 show a side view of a schematic illustration of a light-emitting device.

REFERENCE SIGNS 100 light emitting device
1 semiconductor chip
2 phosphor
3 matrix material
4 substrate
5 UV light
6 visible light
7 UV tape
8 thermal tape
9 singulation
10 main surface
11 side surfaces
12 electrical contact

DETAILED DESCRIPTION

Our light-emitting device may comprise a semiconductor chip. The semiconductor chip may have a main radiation surface. The main radiation surface emits UV light or at least UV light in operation. The light-emitting device may comprise a phosphor. The phosphor may be arranged in the radiation beam of the UV light. The phosphor absorbs in operation at least partially the UV light and converts the UV light, in particular the absorbed UV light, into visible light. Therefore, the device emits mixed light comprising the UV light as well as the visible light.

The light-emitting device may be a light-emitting diode, in particular an inorganic light-emitting diode (LED).

We found that the described light-emitting device has advantageous properties for use in medical applications.

The light emitting device, in particular the light-emitting diode, comprises a semiconductor chip and at least one phosphor. This arrangement can also be called a phosphor integrated LED that is able to emit visible light, for example, white light around the semiconductor chip. The semiconductor chip can be a UV LED. Therefore, the light-emitting device alerts the user when the UV LED is turned on with visible light around the UV LED since UV light is invisible to the user.

The light-emitting device may comprise one or a plurality of semiconductor chips. The semiconductor chip(s) comprise(s) at least one semiconductor layer sequence. The semiconductor layer sequence is preferably based on a III-V compound semiconductor material. The semiconductor material is, for example, a nitride compound semiconductor material such as $Al_nIn_{1-n-m}Ga_mN$ or a phosphide compound semiconductor material such as $Al_nIn_{1-n-m}Ga_mP$ or an arsenide compound semiconductor material such as $Al_nIn_{1-n-m}Ga_mAs$, wherein $0 \leq n \leq 1$, $0 \leq m \leq 1$ and $n+m \leq 1$. In this example, the semiconductor layer sequence can comprise dopants and additional constituents. For the sake of simplicity, however, only the essential constituents of the crystal lattice of the semiconductor layer sequences, that is to say Al, As, Ga, In, N or P, are indicated, even if they can be replaced and/or supplemented in part by small amounts of further substances.

The semiconductor layer sequence comprises one or a plurality of active layers. The at least one active layer generates an electromagnetic radiation, also called light.

By way of example, the active layer includes at least one pn-junction or at least one quantum well structure. In particular, the ultraviolet, visible and/or near infrared radiation is/are generated in the active layer during operation of the semiconductor chip. The radiation generated in the active layer has a peak wavelength. The peak wavelength is that wavelength at which the highest radiation intensity is generated during operation as intended.

The semiconductor chip may have a main radiation surface. The main radiation surface may be arranged perpendicular to the growth direction of the semiconductor layer sequence of the semiconductor chip. The semiconductor chip may emit UV light via the main radiation surface in operation.

The wavelength or the peak wavelength of the UV light may be 280 nm to 380 nm, in particular 315 nm to 380 nm, for example, 360 nm.

The light-emitting device may comprise at least one phosphor or a mixture of at least two phosphors. The phosphor may be arranged in the radiation beam of the UV light. In particular, the semiconductor chip also comprises, beside the main radiation surface, side surfaces arranged perpendicular to the main radiation surface. The UV light may be emitted in particular via the main radiation surface and the side surfaces. The phosphor may be in particular arranged at the side surfaces. The phosphor partially absorbs the UV light and converts the UV light or the absorbed UV light into visible light.

The light-emitting device emits mixed light comprising UV light as well as the visible light. In other words, the mixed light is the sum of the emitted UV light and the emitted visible light.

The semiconductor chip may have side surfaces arranged perpendicular to the main radiation surface, wherein the phosphor is arranged at the side surfaces, and a maximum of 40 percent of the UV light is absorbed and a maximum of 5 percent of the absorbed UV light is converted into visible light by the phosphor.

The semiconductor chip may have side surfaces, in particular four side surfaces if the semiconductor chip is a cube or cuboid. The side surfaces may be arranged perpendicular to the main radiation surface. In particular, the phosphor may be arranged at the side surfaces. In particular, the phosphor may be a layer. The phosphor layer has in particular a thickness of 10 µm, 20 µm, 30 µm, 40 µm, 50 µm, 60 µm, 70 µm, 80 µm, 90 µm or 100 µm as the lower limit to 0.2 mm, 0.5 mm, 1 mm or 2 mm as the upper limit.

A maximum of 40% or 30% or 20% or 10% of the UV light is absorbed by the phosphor. Additionally a maximum of 1%, 2%, 3%, 4%, 5%, 10%, 15%, 20%, 25% or 30% or 35% of the absorbed UV light is converted into visible light by the at least one phosphor.

The light-emitting device may comprise two phosphors. In particular, the phosphors emit light with different peak wavelengths. For example, the first phosphor emits blue or green light and the second phosphor emits red or orange light.

The semiconductor chip may be arranged on a substrate. The substrate may in particular be a growth substrate of the semiconductor layer sequence. A possible material for the substrate can be gallium arsenide, germanium or sapphire.

A maximum of 30% of the UV light may be absorbed by the phosphor. In particular, a maximum of 20% or 10% or 5% or 1% of the UV light is absorbed by the phosphor.

A maximum of 1%, 2% or 3% of the absorbed UV light may be converted into visible light by the phosphor.

The device may emit UV light as well as visible light at the same time in operation.

The device may emit in operation the UV light over the main radiation surface, wherein the semiconductor chip comprises side surfaces embedded by the phosphor, and the device emits in operation the visible light via the side surfaces.

The visible light may be white light. White light can be produced by mixing red, blue and green light and/or varying intensities of the individual red, blue and green emitted semiconductor materials or phosphors.

The visible light may be red, green or blue light.

The phosphor or the at least one phosphor may form a frame around the side surface of the semiconductor chip. The frame can have a thickness of 10 µm, 20 µm, 30 µm, 40 µm, 50 µm, 60 µm, 70 µm, 80 µm, 90 µm or 100 µm as the lower limit to 0.2 mm, 0.5 mm, 1 mm or 2 mm as the upper limit.

The phosphor may partially convert the absorbed UV light (partial conversion). In contrast to partial conversion, full conversion can mean that, in operation, the device solely emits light that is converted by the phosphor.

The phosphor may directly border the side surfaces of the device. In this context "directly borders" means that no further layers or elements are arranged between the phosphor or the phosphor layer and the side surfaces of the device.

The phosphors, or the at least one phosphor may be embedded in an organic matrix material. An organic matrix material can be, for example, silicone or epoxy resin. The phosphor can be embedded homogenously in the organic matrix material. Alternatively, the phosphor can have the concentration gradient in the organic matrix material. The phosphor can be a layer or an element like a frame. In particular, the phosphor forms a frame around the side surfaces of the semiconductor chip. The layer can have a homogenous layer thickness of 10 µm, 20 µm, 30 µm, 40 µm, 50 µm, 60 µm, 70 µm, 80 µm, 90 µm or 100 µm as the lower limit to 0.2 mm, 0.5 mm, 1 mm or 2 mm as the upper limit.

The phosphor may be selected from the group consisting of $Eu^{2+}$-doped nitrides such as $(Ca,Sr)AlSiN_3:Eu^{2+}$, $Sr(Ca,Sr)Si_2Al_2N_6:Eu^{2+}$, $(Sr,Ca)AlSiN_3*Si_2N_2O:Eu^{2+}$, $(Ca,Ba,Sr)_2Si_5N_8:Eu^{2+}$, $(Sr,Ca)[LiAl_3N_4]:Eu^{2+}$; garnets from the general system $(Gd,Lu,Tb,Y)_3(Al,Ga,D)_5(O,X)_{12}:RE$ with X=halide, N or divalent element, D=tri- or tetravalent element and RE=rare earth metals such as $Lu_3(Al_{1-x}Ga_x)_5O_{12}:Ce^{3+}$, $Y_3(Al_{1-x}Ga_x)_5O_{12}:Ce^{3+}$; $Eu^{2+}$-doped sulfides such as $(Ca,Sr,Ba)S:Eu^{2+}$; $Eu^{2+}$-doped SiONs such as $(Ba,Sr,Ca)Si_2O_2N_2:Eu^{2+}$; SiAlONs for instance from the system $Li_xM_yLn_zSi_{12-(m+n)}Al_{(m+n)}O_nN_{16-n}$; beta-SiAlONs from the system $Si_{6-x}Al_zO_yN_{8-y}:RE_z$; nitrido-orthosilicates such as $AE_{2-x-a}RE_xEu_aSiO_{4-x}N_x$, $AE_{2-x-a}RE_xEu_aSi_{1-y}O_{4-x-2y}N_x$ with RE=rare earth metal and AE=alkaline earth metal; orthosilicates such as $(Ba,Sr,Ca,Mg)_2SiO_4:Eu^{2+}$; chlorosilicates such as $Ca_8Mg(SiO_4)_4Cl_2:Eu^{2+}$; chlorophosphates such as $(Sr,Ba,Ca,Mg)_{10}(PO_4)_6Cl_2:Eu^{2+}$; BAM luminescent materials from the $BaO-MgO-Al_2O_3$ system such as $BaMgAl_{10}O_{17}:Eu^{2+}$; halophosphates such as $M_5(PO_4)_3(Cl,F):(Eu^{2+},Sb^{3+},Mn^{2+})$; SCAP luminescent materials such as $(Sr,Ba,Ca)_5(PO_4)_3Cl:Eu^{2+}$. The phosphors or luminescent materials stated in EP 2 549 330 A1 may also be used. With regard to the luminescent materials used, the subject matter of EP 2 549 330 A1 is incorporated herein by reference. "Quantum dots" may moreover also be introduced as phosphors. Quantum dots in the form of nanocrystalline materials which contain a group II-VI compound and/or a group III-V compound and/or a group IV-VI compound and/or metal nanocrystals, are preferred.

In principle, our devices and methods are not specific to the above mentioned type of phosphors. Any phosphors that absorb UV light and emit visible light is suitable. This includes all traditional phosphors used in fluorescent lamps and any white LED exited from UV LED The UV light may have a different main emission direction compared to the main emission direction of the visible light.

The light emitting device may comprise a filter material. The filter material may absorb the UV light not converted into visible light and emitted via the side surface. The filter material can be any UV absorbing filter material.

The visible light may serve as an indicator showing the operational capability of the device for the user.

The device may be used in medical applications. Ultraviolet light has a huge number of useful applications in modern medicine such as disinfection, decontamination of surfaces, drug detection, forensic analysis, light therapy in medicine, and curing polymers. Since UV light is usually invisible and may cause danger to humans, especially during unintentional exposure, there are always safety concerns with modern UV medical applications.

We also provide a method of producing a light-emitting device. Preferably a light-emitting device as specified in conjunction with one or more of the examples mentioned above is produced by the method. Therefore, features of the method are also disclosed for the light-emitting device and vice versa.

The method may comprise at least or exclusively the following steps:
A) applying at least two semiconductor chips on a substrate, each of the two semiconductor chips having a main radiation surface and side surfaces,
B) applying a UV tape on the main radiation surfaces,
C) filling a phosphor between neighboured semiconductor chips so that the phosphor forms a frame around the side surfaces of each semiconductor chip,
D) removing the UV tape, and
E) singulating the assembly mentioned in D) or C).

The phosphor may be embedded in an organic matrix material and the organic matrix material with the phosphor is cured after C).

A thermal tape may be arranged between the semiconductor chips and the substrate.

The phosphor may partially convert the UV light into visible light.

We further provide a light-emitting device. Furthermore, features of the above-mentioned method and the above-mentioned light-emitting device are also disclosed for the following light-emitting device and vice versa.

The light-emitting device may comprise a semiconductor chip having a main radiation surface that emits UV light in operation. The light-emitting device comprises a second semiconductor chip that emits visible light in operation. The light-emitting device emits mixed light comprising the light of the first semiconductor chip (the UV light) as well as the light of the second semiconductor chip (the visible light). In particular, the first and second semiconductor chips are embodied as a light-emitting diode. We also found out that instead of using one phosphor integrated in a semiconductor chip which emits UV light (UV LED), two semiconductor chips, in particular two light-emitting diodes (one UV LED and one visible LED) can solve UV safety concerns.

The second semiconductor chip may comprise a semiconductor layer sequence that generates visible light. When in proper use, the semiconductor layer sequence generates colored or white light. The semiconductor layer sequence may optionally additionally generate a fraction of the radiation in the ultraviolet and/or in the near infrared region of the spectrum. The visible region of the spectrum is considered in particular to be the wavelength of 400 nm to 720 nm inclusive. The semiconductor layer sequence preferably comprises a light-emitting diode layer sequence.

The first and/or second semiconductor chip may comprise at least one semiconductor layer sequence. The semiconductor layer sequence is preferably based on a III-V compound semiconductor material. The semiconductor material is, for example, a nitride compound semiconductor material such as $Al_n In_{1-n-m} Ga_m N$ or a phosphide compound semiconductor material such as $Al_n In_{1-n-m} Ga_m P$ or an arsenide compound semiconductor material such as $Al_n In_{1-n-m} Ga_m As$, wherein $0 \le n \le 1$, $0 \le m \le 1$ and $n+m \le 1$. In this example, the semiconductor layer sequence can comprise dopants and additional constituents. For the sake of simplicity, however, only the essential constituents of the crystal lattice of the semiconductor layer sequences, that is to say Al, As, Ga, In, N or P, are indicated, even if they can be replaced and/or supplemented in part by small amounts of further substances.

UV light generated from UV LED is dangerous as it is not visible to human eyes. Phosphors are added so that part of the light is converted to visible light as indicators. Single UV chips or plurality can be used. There could be more than 1 chip in a module for higher power UV systems.

A light-emitting device and a method of producing a light-emitting device described herein are explained in greater detail below on the basis of examples with reference to the drawings. Identical reference signs indicate identical elements in the individual figures. Relations to scale are not illustrated. Rather individual elements may be illustrated with an exaggerated size to enable a better understanding.

FIG. 1 shows a light-emitting device. The light-emitting device 100 comprises a semiconductor chip 1 having a main radiation surface 10 that emits UV light 5 in operation.

The semiconductor chip 1 comprises side surfaces 11. The light-emitting device 100 comprises a phosphor 2 that is in direct contact with the side surfaces 11 of the semiconductor chip 1.

In particular, the phosphor 2 completely coverts the side surfaces 11 of the semiconductor chip 1.

Alternatively, the phosphor 2 partially coverts the side surfaces 11 of the semiconductor chip 1 (not shown).

The phosphor 2 is arranged in the radiation beam of the UV light 5 and absorbs at least partially the UV light 5 and converts the absorbed UV light into visible light 6.

The device emits mixed light comprising UV light 5 as well as visible light 6. In particular, the light-emitting device emits UV light 5 as well as visible light 6 at the same time.

In particular, the main directions of the visible light 6 and the UV light 5 are different. In particular, the visible light 6 is emitted via the side surfaces 11 of the semiconductor chip 1. The UV light 6 is emitted via the main surface 10 of the semiconductor chip 1.

Therefore, the light-emitting device alerts the user when the semiconductor chip 1 is turned on because the visible light 6 around the semiconductor chip 1 emits light at the same time when the UV light 5 is emitted in operation. The UV light 5 is invisible to the user.

Optionally, the light-emitting device or the semiconductor chip 1 of the light-emitting device 100 is arranged on a substrate 4, for example, gallium arsenide.

Figure 2:
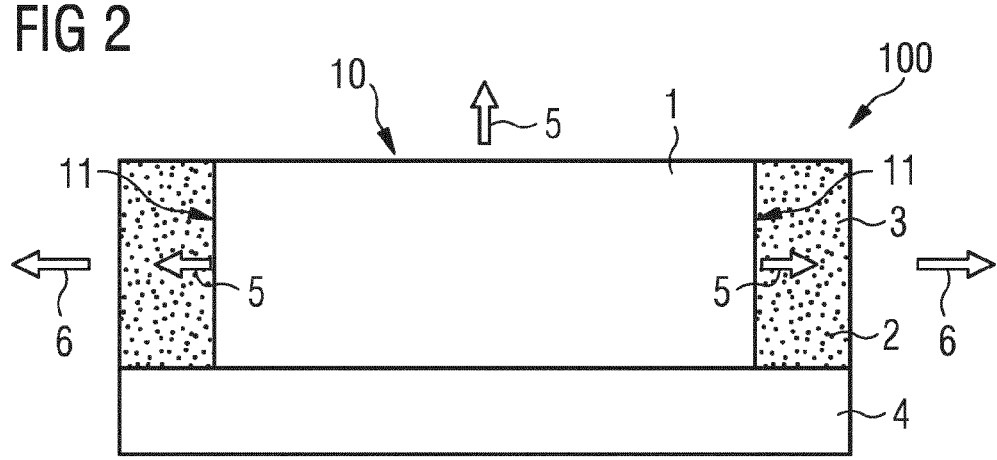

FIG. 2 shows a side view of a schematic illustration of a light-emitting device 100.

The light-emitting device 100 optionally comprises a substrate 4 on which a semiconductor chip 1 is arranged. The side surfaces 11 of the semiconductor chip 1 are completely in direct contact with the phosphor 2.

The phosphor 2 is embedded in an organic matrix material 3, for example, silicone. The semiconductor chip 1 emits UV light 5 via the main radiation surface 10 and the side surfaces 11. The UV light 5 emitted via the side surfaces 11 is partially absorbed by the phosphor 2 and is converted into visible light 6 by the phosphor. Therefore, the light-emitting device 100 emits UV light 5, in particular over the main radiation surface 10 as well as visible light 6 in particular over the side surfaces 11.

Therefore, if a user turns on the light-emitting device 100, the invisible UV light as well as the visible light can be seen by the user. Therefore, the visible light is the indicator for the UV light. Since UV light is usually invisible and could cause danger to humans, especially during unintentional exposure, there are always safety concerns with modern UV medical applications. In particular, the eyes of the user are protected by the light-emitting device 100.

FIGS. 3A to 3F show a method of producing a light-emitting device 100.

Figure 3A:
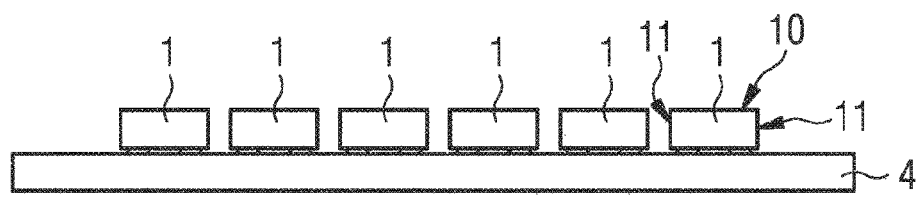
FIGS. 3A to 3F and 4A to 4F show a schematic illustration of a method of producing a light-emitting device.

FIG. 3A shows a substrate 4 on which at least two semiconductor chips 1, here six semiconductor chips, are arranged. Each of the semiconductor chips 1 has a main radiation surface 10 facing away from the substrate 4 and side surfaces.

Figure 3B:
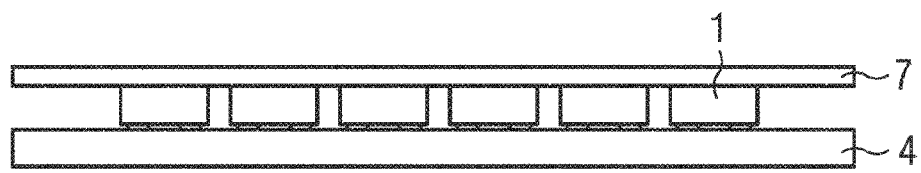

After applying the semiconductor chips on the substrate 4 as shown in FIG. 3A, a UV tape 7 is applied on the main radiation surface of each of the semiconductor chips as shown in FIG. 3B. In particular, one UV tape is arranged on the main radiation surfaces of all semiconductor chips.

Figure 3C:
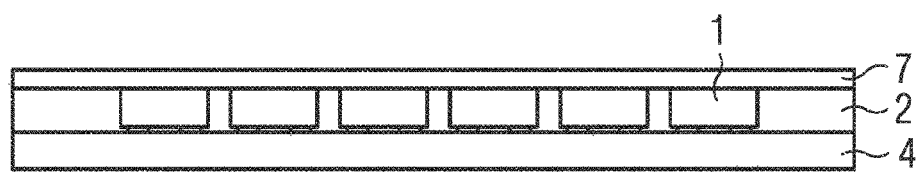

As shown in FIG. 3C, the phosphor 2 is filled between neighboring semiconductor chips 1 so that the phosphor forms a frame around the side surfaces 11 of each semiconductor chip.

Figure 3D:
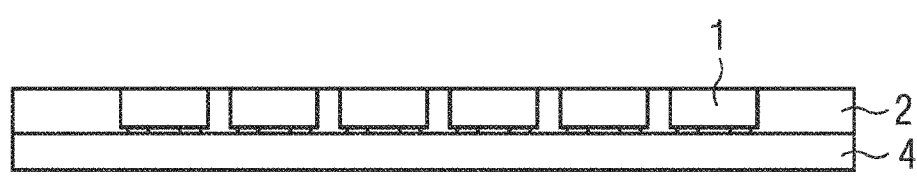
Figure 3E:
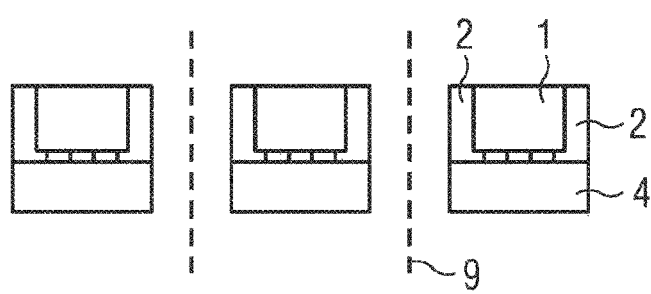
Figure 3F:
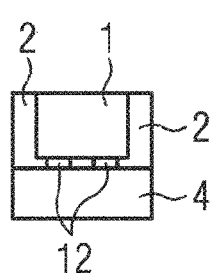

As shown in FIG. 3D, the UV tape 7 is removed. After removing the UV tape 7 the semiconductor chips 1 are singulated 9 as shown in FIG. 3E.

At the end of the method a light-emitting device 100 is produced which comprises a light emitting device comprising a semiconductor chip having a main radiation surface and side surfaces that emit UV light via the main radiation surface in operation, and a phosphor arranged in the radiation beam of the UV light at the side surfaces, absorbs partially the UV light, wherein the phosphor converts the UV light into visible light so that the device emits mixed light comprising the UV light as well as visible light, the visible light is emitted via the side surfaces and the UV light is emitted via the main radiation surface, and the visible light is an indicator showing the operational capability of the device for the user. In this example, the light-emitting device comprises a substrate 4, a semiconductor chip 1 having two electrical contacts 12 and a frame of phosphor 2 arranged directly on the side surfaces 11 of the semiconductor chip 1.

FIGS. 4A to 4F show a method of producing a device.

Figure 4A:
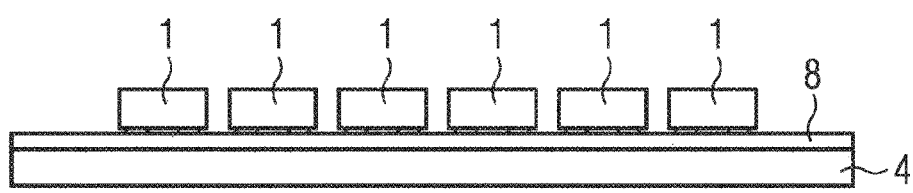

According to FIG. 4A, a thermal tape 8 is arranged on the substrate 4. Semiconductor chips 1 are arranged on the thermal tape 8.

Figure 4B:
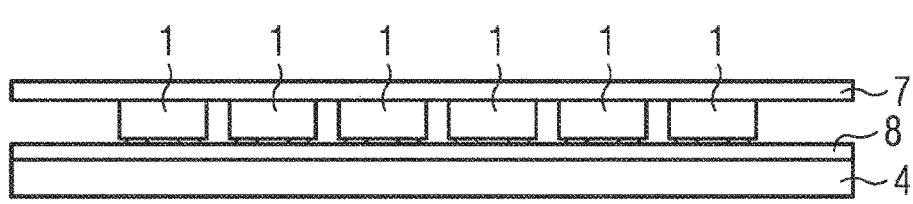

As shown in FIG. 4B, a UV tape 7 is applied on the main radiation surfaces 10 of the semiconductor chips 1.

Figure 4C:
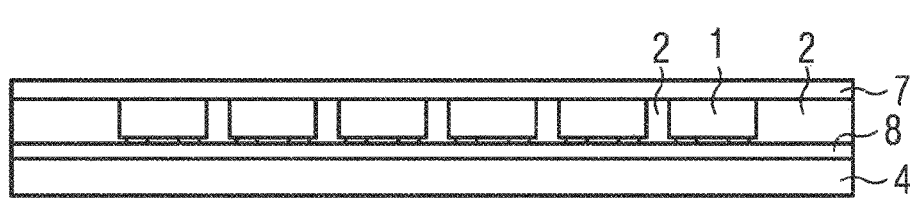

As shown in FIG. 4C, the phosphor 2 is filled between neighboring semiconductor chips 1 so that the phosphor forms a frame around the side surfaces 11 of each semiconductor chip 1.

Figure 4D:
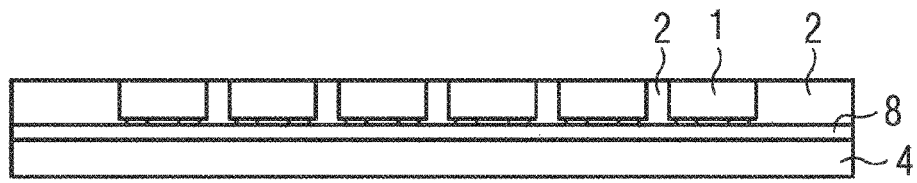
Figure 4E:
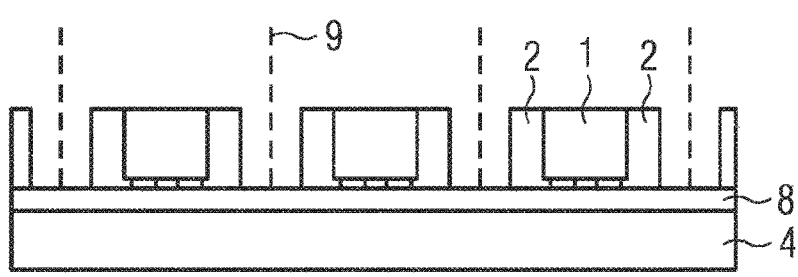

As shown in FIG. 4D, the UV tape is removed and the assembly as produced in FIG. 4D is singulated 9.

In particular, the thermal tape 8 and the substrate 4 are not singulated.

Figure 4F:
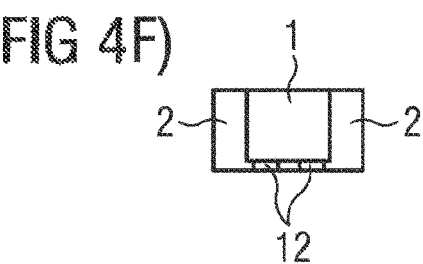

As shown in FIG. 4F, the method produces a light-emitting device 100 comprising a semiconductor chip 1 and a phosphor 2 and electrical contacts 12. In contrast to the device of FIG. 3F, the light-emitting device 100 of FIG. 4F does not comprise a substrate 4. In other words, the light-emitting device 100 of FIG. 4F is free of a substrate 4.

We found that only one semiconductor chip is needed to emit UV light and visible light. A small package footprint is possible. The emission of visible light around the UV LED can further improve the safety factor of modern medical applications.

Our devices and methods as described herein are not restricted by the description on the basis of the examples. Rather, this disclosure encompasses any novel features and also any combination of features that in particular includes any combination of features in the appended claims even if the feature or combination is not explicitly specified in the claims or examples.

The invention claimed is:

1. A light emitting device comprising:
 a semiconductor chip having a main radiation surface and side surfaces that emit UV light via the main radiation surface in operation, and
 a phosphor arranged in the radiation beam of the UV light at the side surfaces, absorbs partially the UV light,
 wherein the phosphor converts the UV light into visible light so that the device emits mixed light comprising the UV light as well as visible light,
 the visible light is emitted via the side surfaces and the UV light is emitted via the main radiation surface, and
 the visible light is an indicator showing the operational capability of the device for the user.

2. The light emitting device according to claim 1,
 wherein the semiconductor chip has side surfaces arranged perpendicular to the main radiation surface,
 the phosphor is arranged at the side surfaces, and
 a maximum of 40 percent of the UV light is absorbed and a maximum of 5 percent of the absorbed UV light is converted into visible light by the phosphor.

3. The light emitting device according to claim 1, wherein the semiconductor chip is arranged on a substrate.

4. The light emitting device according to claim 1, wherein a maximum of 30 percent of the UV light is absorbed by the phosphor.

5. The light emitting device according to claim 4, wherein a maximum of 3 percent of the absorbed UV light is converted into visible light by the phosphor.

6. The light emitting device according to claim 1, wherein the device emits UV light as well as visible light at the same time in operation.

7. The light emitting device according to claim 1 that emits, in operation, the UV light over the main radiation surface, wherein the semiconductor chip comprises side surfaces embedded by the phosphor, and the device emits in operation the visible light via the side surfaces.

8. The light emitting device according to claim 1, wherein the visible light is white light.

9. The light emitting device according to claim 1, wherein the visible light is red, green or blue light.

10. The light emitting device according to claim 1, wherein the wavelength of the UV light is 280 nm and 380 nm.

11. The light emitting device according to claim 1, wherein the phosphor forms a frame around the side surfaces of the semiconductor chip.

12. The light emitting device according to claim 1, wherein the phosphor directly borders the side surfaces of the device.

13. Light emitting device according to claim 1, wherein the phosphor is selected from the group consisting of $Eu^{2+}$-doped nitrides, garnets, $Eu^{2+}$-doped sulfides, $Eu^{2+}$-doped SiONs, SiAlONs, beta-SiAlONs, nitrido-orthosilicates, orthosilicates, chlorosilicates, chlorophosphates, BAM luminescent materials, halophosphates, SCAP luminescent materials and Quantum dots.

14. The light emitting device according to claim 1, wherein the phosphor is embedded in an organic matrix material.

15. A medical device comprising the light emitting device according to claim 1.

16. A method of producing a light emitting device comprising:
   A) applying at least two semiconductor chips on a substrate, each of the two semiconductor chips having a main radiation surface and side surfaces,
   B) applying a UV tape on the main radiation surfaces,
   C) filling a phosphor between neighboring semiconductor chips so that the phosphor forms a frame around the side surfaces of each semiconductor chip,
   D) removing the UV tape, and
   E) singulating the assembly.

17. The method according to claim 16, wherein the phosphor is embedded in an organic matrix material and the organic matrix material with the phosphor is cured after C).

18. The method according to claim 16, wherein a thermal tape is arranged between the semiconductor chips and the substrate.

19. The method according to claim 17, wherein a thermal tape is arranged between the semiconductor chips and the substrate.

* * * * *